(12) United States Patent
Luzon et al.

(10) Patent No.: US 9,271,755 B2
(45) Date of Patent: Mar. 1, 2016

(54) MINUTELY CONTROLLED DERMABRASION HAND PIECE AND A METHOD FOR CONTROLLING THEREOF

(71) Applicant: Derma Dream Group Ltd., Tortola (VG)

(72) Inventors: Yosef Luzon, Bet Yehoshua (IL); Martin Gurovich, Tel Aviv (IL)

(73) Assignee: DERMA DREAM GROUP LTD., Road Town Tortola (VG)

( * ) Notice: Subject to any disclaimer, the term of this patent is extended or adjusted under 35 U.S.C. 154(b) by 403 days.

(21) Appl. No.: 13/653,432

(22) Filed: Oct. 17, 2012

(65) Prior Publication Data

US 2013/0138119 A1 May 30, 2013

Related U.S. Application Data

(60) Provisional application No. 61/564,056, filed on Nov. 28, 2011.

(51) Int. Cl.
*A61B 17/50* (2006.01)
*A61B 17/54* (2006.01)

(52) U.S. Cl.
CPC .................................... *A61B 17/54* (2013.01)

(58) Field of Classification Search
CPC ............... A61M 35/003; A61B 17/54; A61B 2017/00535; A61B 2017/320012
USPC ................................................... 606/131–133
See application file for complete search history.

(56) References Cited

U.S. PATENT DOCUMENTS 5,562,603 A * 10/1996 Moll et al. .................... 600/204
6,629,983 B1 * 10/2003 Ignon ............................ 606/131

* cited by examiner

*Primary Examiner* — Victor Nguyen
(74) *Attorney, Agent, or Firm* — Pearl Cohen Zedek Latzer Baratz LLP

(57) ABSTRACT

A minutely controlled dermabrasion hand piece includes a main hand piece body for holding the hand piece by a user, a treatment head to provide negative pressure to a treated tissue and a vacuum tube to provide negative pressure to the treatment head through the main hand piece body. The main hand piece body includes at least one opening to control the supply of negative pressure to the treatment head. The opening is blockable by the user holding the hand piece.

10 Claims, 4 Drawing Sheets

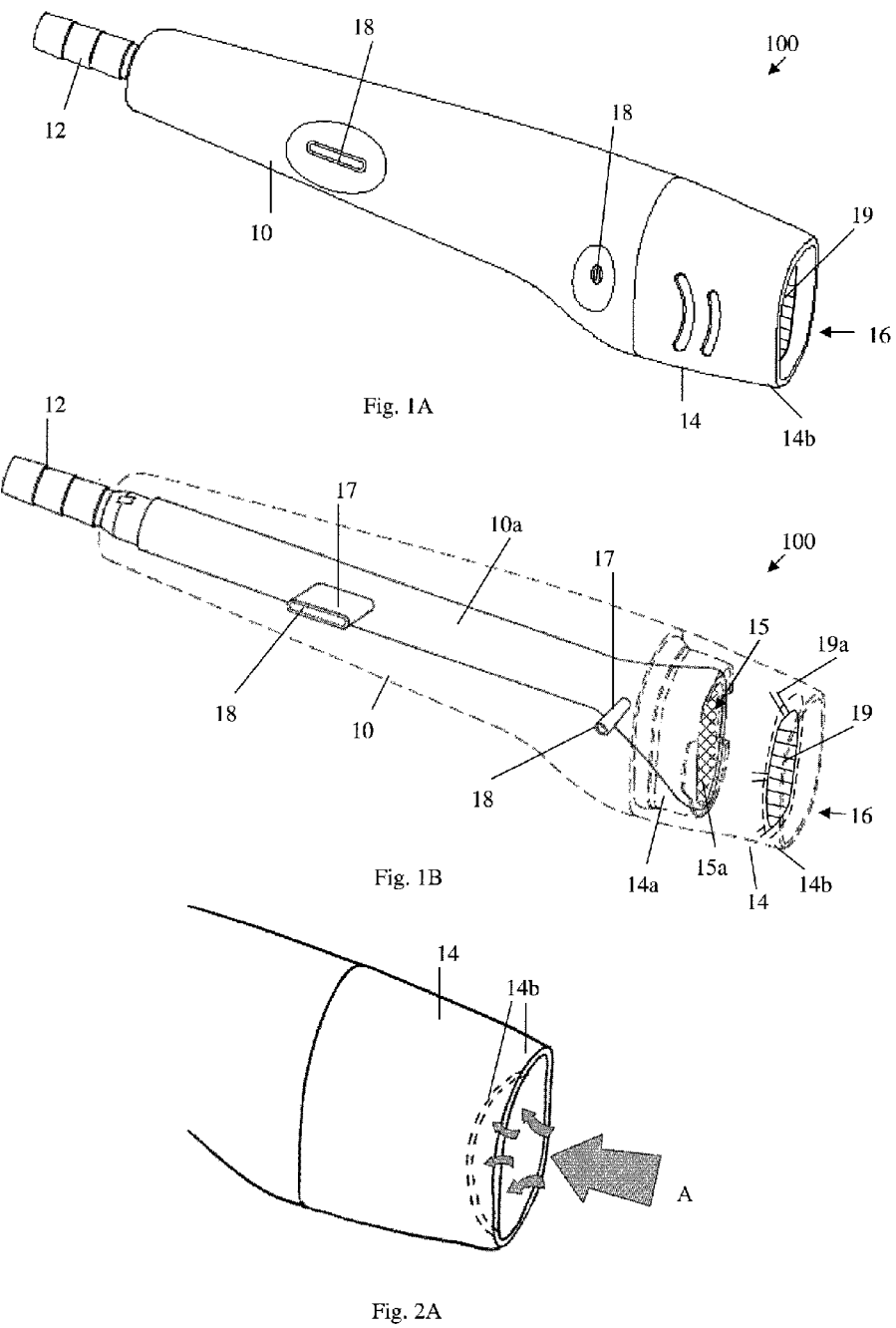

MINUTELY CONTROLLED DERMABRASION HAND PIECE AND A METHOD FOR CONTROLLING THEREOF

CROSS REFERENCE TO RELATED APPLICATIONS

This Application claims the benefit of U.S. Provisional Application Ser. No. 61/564,056, filed Nov. 28, 2011, which is hereby incorporated by reference in its entirety.

BACKGROUND OF THE INVENTION

Cosmetic skin dermabrasion is a rapidly growing field and many dermabrasion devices are aimed for skin treatments by professionals. Some dermabrasion devices are aimed for use by domestic users. However, since dermabrasion devices for domestic users are usually used without medical observation, more regard to safety, efficiency, and self-use comfort should be paid in their design.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

FIGS. 1A and 1B are opaque and partially see-through illustrations of a dermabrasion hand piece according to some embodiments of the present invention;

FIGS. 2A, 2B and 2C are schematic illustrations of a treatment head with flexible elastic rim according to embodiments of the present invention;

Figure 2B:
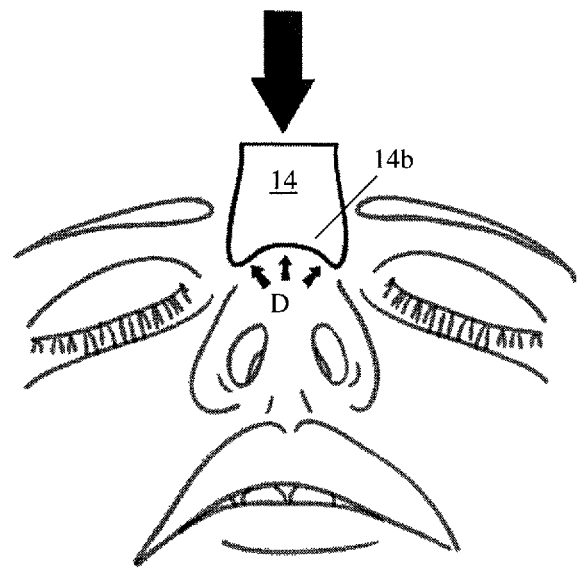

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Reference is now made to FIGS. 1A and 1B, which are opaque and partially see-through illustrations of a dermabrasion hand piece 100 according to some embodiments of the present invention. Dermabrasion hand piece 100 may include a main hand piece body 10, a vacuum tube 12, a treatment head 14 and a treatment abrasive layer 19. Main body 10 may be designated for handling of the hand piece by a user, for example by holding the hand piece at the main body 10 and maneuvering treatment head 14 over a treated skin area of the user himself or of another person. Treatment head 14 may be installed, for example removably installed, on a distal end of main body 10. Vacuum tube 12 may provide negative pressure through main body 10 to treatment head 14 from a vacuum source. Treatment head 14 may include an opening 16 through which the negative pressure may be provided to a treated tissue. Abrasive layer 19 may be installed, for example removably installed, within treatment head 14 in proximity to opening 16, so that when negative pressure is applied to a tissue, the tissue is sucked into opening 16 and dermabrasion my be applied to the tissue by abrasive layer 19. For example, abrasive layer 19 may be installed within treatment head 14 so that a gap is established around abrasive layer 19 between the inner perimeter of head 14 and the outer perimeter of layer 19 and thus, for example, negative pressure may be provided to the treated tissue from around abrasive layer 19. However, the invention is not limited in that respect and negative pressure may be provided to the treated tissue through the abrasive layer or in any other suitable configuration. Abrasive layer 19 may be installed in treatment head 14, for example, by a suitable number of ribs 19a or by any other suitable manner.

As shown in FIG. 1B, main body 10 may include an internal tube 10a, which may be continuously connected in one end to vacuum tube 12 for supply of negative pressure. Internal tube 10a may end with an opening 15 to supply the negative pressure into internal space of treatment head 14 and towards the treated issue through opening 16, for example from around abrasive layer 19. Opening 15 may include a filter 15a to prevent large waste particles from entering and/or blocking internal tube 10a and/or tube 12. The filter may be replaceable or removable.

In some embodiments of the present invention, main body 10 may include channels 17 that end with openings 18. When openings 18 are not blocked, the provided negative pressure may exit out of openings 18 and therefore may not be applied on the treated tissue. The supply of negative pressure from vacuum tube 12 to treatment head 14 may be controlled by a user by blocking and/or opening openings 18 for example by the user's hand and/or fingers. This may enable easy, quick and intuitive control of the applied vacuum. Openings 18 may operate as safety mechanism during the treatment, giving an alternate exit path for the negative pressure, other than the treated surface. Only when openings 18 are blocked during the intuitive and regular handling by the user, the alternate path is blocked and, for example, the negative pressure may affect the treated surface. Therefore, controlling of the supply of negative pressure to treatment head 14 may be performed by selectively blocking openings 18 by the user. It will be appreciated that although the drawings show two openings 18, the invention is not limited in that respect and hand piece 100 may include one opening 18 or any other suitable number of openings 18 in any suitable shapes and sizes.

Referring to FIG. 2A, Treatment head 14 may be formed of or include one or more elastic material such as, for example silicone compounds, rubber, elastomer, polymer, polyurethane and/or any other suitable elastic material. Treatment head 14 may include an elastic wrapping sleeve 14a and/or a flexible rim 14b. Wrapping sleeve 14a may wrap a portion of main body 10, for example an edge of main body 10 and/or of internal tube 10a and thus, for example, treatment head 14 may be installed and/or tightly gripped on main body 10 by elastic wrapping sleeve 14a. Other manners of connection between treatment head 14 and main body 10 are possible.

Figure 2C:
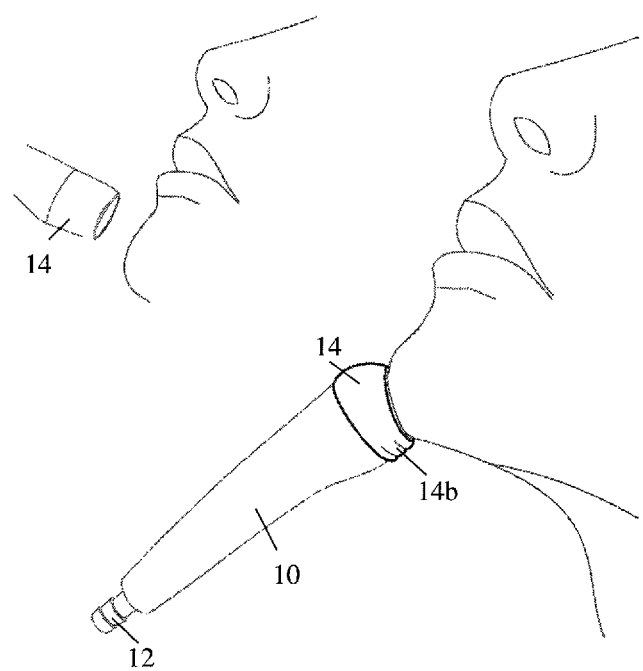

Flexible rim 14b may be elastically adaptable to the shape of the treated surface as described in detail herein with reference to FIGS. 2A, 2B and 2C.

Some curved body areas such as, for example, chin, nose and other areas, may be difficult to treat with rigid treatment heads because a rigid treatment head usually can't be sealingly attached to the curved treated surface and therefore, a negative pressure cannot be effectively applied to the tissue. By elastic adaptation of rim 14b or the entire treatment head 14 to the shape of the treated surface, a better sealing may be obtained between the treated surface and treatment head 14 and thus, for example, a better effectivity and/or efficiency of the applied negative pressure. Reference is now made to FIGS. 2A, 2B and 2C, which are schematic illustrations of treatment head 14 with flexible elastic rim 14b according to embodiments of the present invention. As shown in FIG. 2A, a pressure may be applied on rim 14b, for example in the direction of arrow A. The pressure may be applied, for example, by a treated body portion onto which treatment head 14 may be pressed in order to provide a treatment. The pressure applied on rim 14b may cause elastic deformation of flexible rim 14b and, thus, for example, may adapt the shape of rim 14b, for example as shown by the dashed lines, to the shape of the treated surface. For example, as shown in FIG. 2B, the shape of treatment head 14 may be adapted to the shape of a treated surface, for example in the nose area, as result of the pressure applied by the treated curved surface on flexible rim 14b (in the direction shown by the arrows D) when treatment head 14 is pressed onto the treated curved area. Similarly, as shown in FIG. 2C, the shape of treatment head 14 may be adapted to the shape of, for example, the chin area, as result of the pressure applied by the curved chin surface on flexible rim 14b when treatment head 14 is pressed onto the treated curved surface. In some embodiments, abrasive layer 19 may also be flexible, rotatable and/or spring steerable and thus, for example, providing extra flexibility to hand piece 100 and enabling maximal adjustment to the shape of the treated surface.

Naturally, certain body portions have different angles and curves which may be harder to treat with a unidirectional hand piece. Ergonomically, it is more comfortable for a user to hold the handle in certain angles than in other angles. Therefore, some embodiments of the present invention may include a bendable articulation section included, for example, in main body 10. The bendable section may enable better comfort on hand piece 100 and/or may facilitate treatment of curved body areas and/or body areas with uncomfortable access, for example by enabling better contact of treatment head 14 with the treated surface.

Figure 3A:
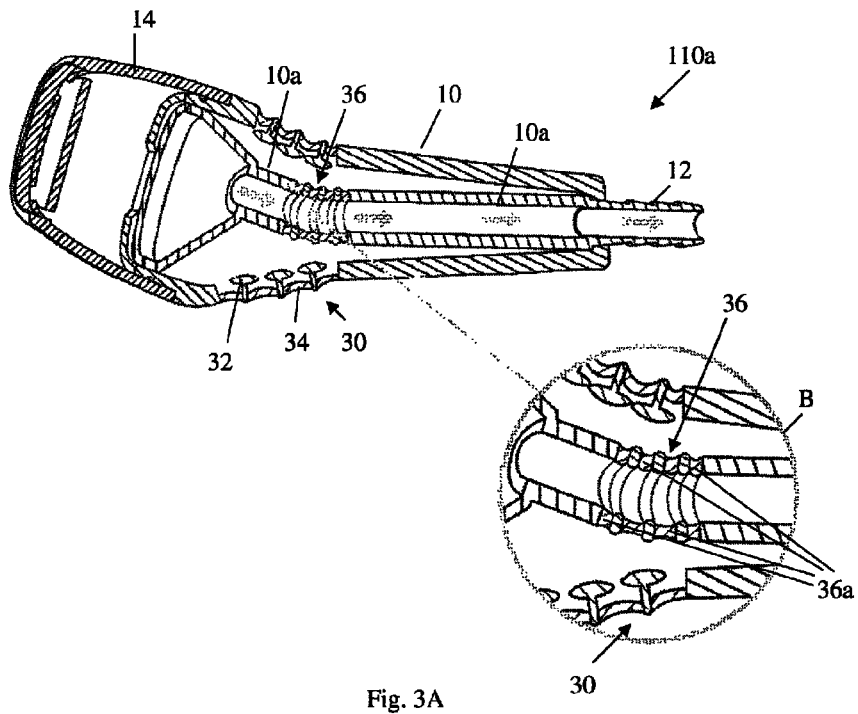
FIGS. 3A and 3B are cross-sectional schematic illustrations of treatment hand pieces with bendable articulation sections according to two different embodiments of the present invention.
Figure 3B:
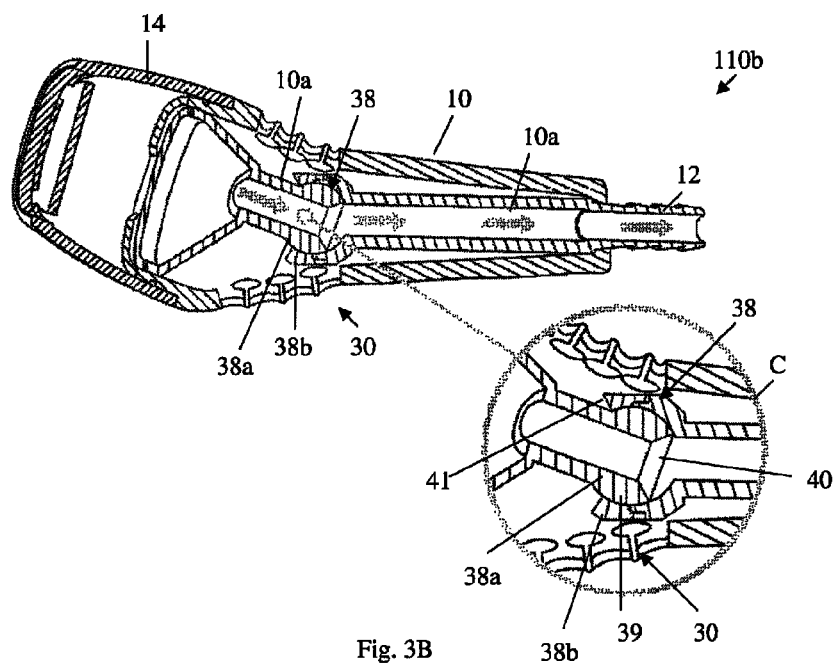

Reference is now made to FIGS. 3A and 3B, which are cross-sectional schematic illustrations of treatment hand pieces 110a and 110b with bendable articulation sections according to two different embodiments of the present invention. In FIGS. 3A and 3B, elements similar to the elements of hand piece 100, described in detail herein, are marked with the same reference number. Hand pieces 110a and 110b include treatment head 14, vacuum tube 12, main body 10 and internal tube 10a. According to some embodiments of the present invention, main body 10 may include articulation section 30. Articulation section 30 may be bendable and/or steerable, for example plastically bendable, so that a certain angle is created in main body 10. The extent of bending/steering, and therefore, for example, the created angle, may be controlled by the user of hand piece 110a or 110b. As shown in FIGS. 3A and 3B, articulation section 30 may be or include, for example, a peripheral/annular accordion joint, which may enable bending of main body 10 in all directions. Articulation section 30 may include around a perimeter of main body 10 alternating peripheral/annular rigid nodes 32 and annular flexible grooves 34, which may form a corrugated pattern that allow bending and/or steering of section 30. For example, each rigid node 32 may be located between two flexible grooves 34. Grooves 34 may enable the bending of articulation section 30. However, the flexibility of grooves 34 may be limited, for example so as to limit the bendability of section 30, i.e. the extent to which section 30 may bend. Additionally, or alternatively, the bendability of section 30 may be limited by rigid nodes 32, which may contact each other and/or press on each other above a certain bending angle, thus preventing further unwanted bending of section 30. Internal tube 10a may include a bendable or steerable section 36 (FIG. 3A) or 38 (FIG. 3B), which may bend/be steered in accordance with the bending of section 30. Bendable sections 30 and 36 are shown more closely in circle B. Bendable sections 30 and 38 are shown more closely in circle C.

As shown in FIG. 3A, internal tube 10a may include, in some embodiments of the present invention, a bendable section 36 having a hollow core that enables continuous passage of negative pressure through internal tube 10a. Bendable section 36 may be or include, for example, an annular accordion joint, which may include annular corrugated pattern of grooves 36a that allow bending of section 36, without blocking the passage of negative pressure through internal tube 10a. The extent to which section 36 may bend may be limited by the flexibility of the annular grooves 36a. According to other embodiments of this invention, internal tube 10a may be implemented as a flexible tube, especially regarding to section 36.

As shown in FIG. 3B, internal tube 10a may include, in some embodiments of the present invention, a steerable section 38 having a hollow core that enables continuous passage of negative pressure through internal tube 10a. Steerable section 38 may allow steering in all directions. For example, steerable section 38 may be or include a ball-and-socket (spheroidal) joint, which may include, for example, a spheroidal joint 38a and a socket joint 38b, wherein spheroidal joint 38a fits into socket joint 38b. Both joints 38a and 38b may include hollow cores that continuously lead to a hollow interior/core of internal tube 10a, so as to allow continuous passage of negative pressure through internal tube 10a. Spheroidal joint 38a may include spheroidal surface 39 bounded and/or cut off by a juncture with internal tube 10a at one end and by an opening 40 towards the hollow core of socket joint 38b and/or internal tube 10a at the other end. Socket joint 38b may include a socket edge 41 to contain and/or hold spheroidal joint 38a. Socket edge 41 may collide with tube 10a when the steering reaches a certain angle and thus, for example, the steering angle may be limited. The steering may be limited so that, for example, the passage of negative pressure through internal tube 10a and through joints 36 and 38 will not be blocked. According to other embodiments of the present invention, the flexible angle of the main body 10 may be also controlled and/or limited by a certain amount of friction between the various articulation parts.

Figure 4:
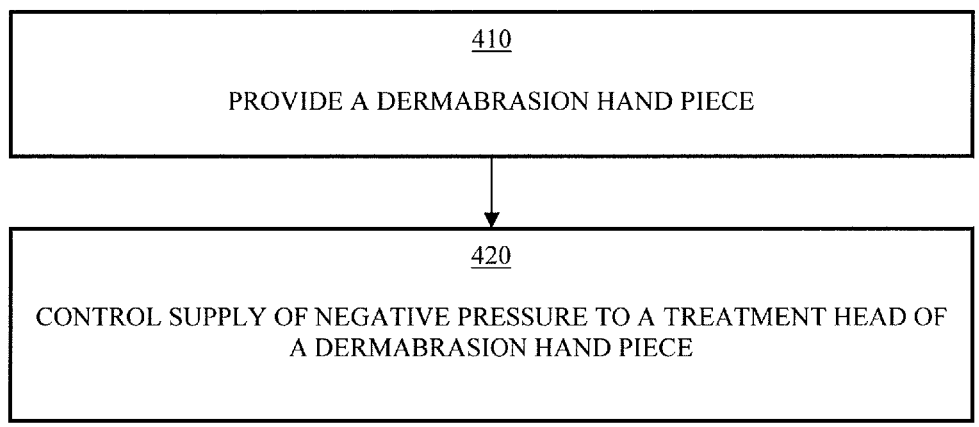
FIG. 4 is a flowchart illustrating a method for minutely controlling a dermabrasion hand piece according to embodiments of the present invention.

Reference is now made to FIG. 4, which is a flowchart illustrating a method for minutely controlling a dermabrasion hand piece according to embodiments of the present invention. As indicated in block 410, the method may include providing a dermabrasion hand piece. As described in detail above, the hand piece may include, for example, a main hand piece body for holding the hand piece by a user and a treatment head to provide negative pressure to a treated tissue and a vacuum tube to provide negative pressure to the treatment head through the main hand piece body. The main hand piece body may include at least one opening to control the supply of negative pressure to the treatment head and the at least one opening may be blockable by a user holding the hand piece.

As indicated in block 420, the method according to embodiments of the present invention may include controlling supply of negative pressure to the treatment head of the dermabrasion hand piece, wherein the controlling of the supply of negative pressure to the treatment head may be performed by selectively blocking the at least one opening.

Additionally, the method according to embodiments of the present invention may include adapting the shape of the treatment head to the shape of the treated surface. As described in detail above, the adaptation may be performed by a flexible rim that may be included in the treatment head and may be adaptable to the shape of the treated surface. Additionally, the method may include controlling an angle created by a bendable articulation section that may be included in the main hand piece body, as described in detail above.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A minutely controlled dermabrasion hand piece, the hand piece comprising:
   a main hand piece body for holding the hand piece by a user, the main hand piece body including a bendable articulation section that comprises a peripheral/annular accordion joint having a corrugated pattern to enable bending of the articulation section, the accordion joint including alternating annular rigid nodes and annular flexible grooves;
   a treatment head to provide negative pressure to a treated tissue through an opening of the treatment head when the opening of the treatment head is placed against the treated tissue; and
   a vacuum tube to provide negative pressure to the treatment head through the main hand piece body,
   wherein the main hand piece body comprises at least one opening that is configured to be selectively blocked and opened by the user to control the supply of negative pressure to the treatment head.

2. The hand piece of claim 1, wherein the treatment head comprises an abrasive layer.

3. The hand piece of claim 2, wherein the treatment head comprises a gap through which negative pressure is providable to the treated tissue, the gap being around the abrasive layer between inner perimeter of the head and outer perimeter of the abrasive layer.

4. The hand piece of claim 1, wherein the treatment head comprises a flexible rim adaptable to the shape of the treated surface.

5. The hand piece of claim 1, wherein said main hand piece body comprises an internal tube through which the negative pressure is passable, and wherein said internal tube comprises a steerable section to steer said internal tube in accordance with the bending of the bendable articulation section of the main hand piece body.

6. The hand piece of claim 5, wherein the steerable section of the internal tube is a bendable section comprising an annular accordion joint.

7. The hand piece of claim 5, wherein the steerable section of the internal tube comprises a spheroidal joint and a socket joint.

8. A method for minutely controlling a dermabrasion hand piece, the method comprising:
   providing a dermabrasion hand piece comprising:
      a main hand piece body for holding the hand piece by a user, the main hand piece body including a bendable articulation section that comprises a peripheral/annular accordion joint having a corrugated pattern to enable bending of the articulation section, the accordion joint including alternating annular rigid nodes and annular flexible grooves;
      a treatment head to provide negative pressure to a treated tissue through an opening of the treatment head when the opening of the treatment head is placed against the treated tissue; and
      a vacuum tube to provide negative pressure to the treatment head through the main hand piece body,
      wherein the main hand piece body comprises at least one opening that is configured to be selectively blocked and opened by user to control the supply of negative pressure to the treatment head; and
   selectively blocking and opening the at least one opening to control supply of negative pressure to said treatment head of said dermabrasion hand piece.

9. The method of claim 8, wherein said treatment head comprises a flexible rim adaptable to the shape of the treated surface, and wherein the method comprises adapting the shape of said treatment head to the shape of the treated surface.

10. The method of claim 8, wherein the method comprises controlling an angle created by said articulation section.

* * * * *